(12) United States Patent
Engman

(10) Patent No.: US 8,328,555 B2
(45) Date of Patent: Dec. 11, 2012

(54) IMPLANT

(75) Inventor: Fredrik Engman, Molnlycke (SE)

(73) Assignee: Neoss Limited (GB)

( * ) Notice: Subject to any disclaimer, the term of this patent is extended or adjusted under 35 U.S.C. 154(b) by 980 days.

(21) Appl. No.: 10/492,709

(22) PCT Filed: Oct. 4, 2002

(86) PCT No.: PCT/GB02/04512
§ 371 (c)(1),
(2), (4) Date: Dec. 6, 2004

(87) PCT Pub. No.: WO03/028579
PCT Pub. Date: Apr. 10, 2003

(65) Prior Publication Data
US 2005/0089818 A1   Apr. 28, 2005

(30) Foreign Application Priority Data
Oct. 4, 2001 (GB) .................................. 0123804.7

(51) Int. Cl.
*A61C 8/00* (2006.01)
(52) U.S. Cl. ...................................................... 433/174
(58) Field of Classification Search .......... 433/173–174; 606/73
See application file for complete search history.

(56) References Cited

U.S. PATENT DOCUMENTS

| | | | | |
|---|---|---|---|---|
| 4,713,004 A | * | 12/1987 | Linkow et al. ............... | 433/174 |
| 4,863,383 A | * | 9/1989 | Grafelmann ................ | 433/174 |
| 5,338,197 A | | 8/1994 | Kwan ........................... | 433/174 |
| 5,427,527 A | | 6/1995 | Niznick et al. ............... | 433/174 |
| 5,527,183 A | * | 6/1996 | O'Brien ....................... | 433/174 |
| 5,902,109 A | | 5/1999 | Reams, III et al. ........... | 433/173 |
| 5,967,783 A | * | 10/1999 | Ura ............................... | 433/174 |
| 6,048,204 A | * | 4/2000 | Klardie et al. ............... | 433/174 |
| 6,068,479 A | | 5/2000 | Kwan ........................... | 433/173 |
| 6,099,312 A | | 8/2000 | Alvaro ......................... | 433/174 |

FOREIGN PATENT DOCUMENTS

| | | |
|---|---|---|
| WO | WO 97/03621 | 2/1997 |
| WO | WO 99/23970 | 5/1999 |
| WO | WO 00/53117 | 9/2000 |
| WO | WO 0053117 A1 * | 9/2000 |

OTHER PUBLICATIONS

International Search Report dated Jan. 13, 2003 for PCT/GB02/04512.

* cited by examiner

*Primary Examiner* — Sunil K Singh
(74) *Attorney, Agent, or Firm* — Akerman Senterfitt

(57) ABSTRACT

An implant for anchoring a tightly fitting prosthesis includes an externally threaded implant body configured to be screwed into bone using an insertion tool, the body having a first end and a second apex end, said first end being provided with an internal open ended axial bore, the implant being tapered such that the apex end is smaller in diameter than the first end where the taper is not greater than 2°. The implant is also provided with an incremental cutting face.

24 Claims, 3 Drawing Sheets

Graph 1 Placement in a Mandible

Graph 2 Placement in a Maxilla

IMPLANT

RELATED APPLICATIONS

The present application is a 35 U.S.C. §371 national phase application of PCT International Application No. PCT/GB02/04512, having an international filing date of Oct. 4, 2002, and claiming priority to Great Britain Patent Application No. 0123804.7, filed Oct. 4, 2001, the disclosures of which are incorporated herein by reference in their entireties. The above PCT International Application was published in the English language and has International Publication No. WO 03/028579 A1.

BACKGROUND OF THE INVENTION

The present invention is directed to a novel implant and to a novel method of treatment related thereto.

In particular the invention relates to a threaded implant intended to be screwed into bone, preferably in the maxilla or mandible as a means of attaching or anchoring a prosthesis.

Current implant design, e.g. dental implant design, has tended be increasingly adapted towards different clinical situations such as placement in soft or hard bone, for example, a certain type of implant may be used for fixing into trabecular or poor quality bone, e.g. soft bone, whereas a different implant may be used for fixing into dense cortical bone or hard tissues. However, there are common features that would be desirably incorporated in an implant design placed in hard bone, like good cutting efficiency and low friction in order to have acceptable level of insertion torque. Meanwhile, there are reasons to have a high insertion torque in situations with soft bone in order to increase the initial stability by additional bone compression. Current systems available to, for example, dental practitioners do not readily lend themselves to these contradictory requirements.

The result of this trend is that there are current implant systems that have separate designs for these situations. One example is the Mk III-implants in the Branemark system (available from Nobel Biocare), which are mainly designed for use in hard bone. Similarly, the Replace system (also available from Nobel Biocare) is specifically designed for use in socket replacement. Alternatively, the Mk IV-implants in the Branemark system (available from Nobel Biocare) are specifically designed for use in soft bone. From this it can be seen that conventional systems utilise a range of types of implant designs for different types of bone quality.

U.S. Pat. No. 5,427,527, to Niznick, et al describes a dental implant system utilising a threaded cylindrical form provided with a plurality of longitudinal channels. In particular, the implant is a conical or tapered threaded implant, that is a lower part of the implant being smaller in diameter than the cylindrical bore hole and the upper part being greater in diameter. More specifically, Niznick describes a method of fixing an implant wherein the diameter of the bore hole is less than the diameter of the implant. However, one particular disadvantage of the Niznick system is that the lower part of the implant is smaller in diameter than the bore hole used, whilst this may make insertion easier, the fixture of the implant has only-limited stability.

U.S. Pat. No. 5,902,109, Reams, et al, describes a reduced friction screw-type dental implant which has a non-circular cross-section, which includes a plurality of lobes and dwells such that on insertion into the bone only the lobes engage with the bone tissue allowing bone to grow into the dwells.

International Patent Application No WO 99/23970 to Björn, et al, describes the Nobel Biocare Branemark Mk-IV system hereinbefore described. Björn describes an implant system which comprises a threaded tapered implant which is provided with a tapered anchoring hole in its upper part. In particular, FIG. 2 of Björn describes an implant provided with cutting edges (5).

U.S. Pat. No. 6,099,312 describes a dental implant member which has a generally longitudinal cylindrical shape wherein the entire length of the implant is provided with double ruled grooves, preferably equidistant from each other.

U.S. Pat. No. 5,338,197 describes a tapered anchor pin for securing an artificial tooth or dental prosthesis to the bone of a patient, having a plurality of cutting flutes disposed about the periphery of a top portion of the pin. However, the pin of the prior art is tapered only to address the problem of a countersinking operation.

In addition, a commercially available implant system from Ha-Ti Dental comprises a generally cylindrical tapered implant with a longitudinal groove which is used by anchoring in a tapered hole.

Thus, it can be seen that there are a number of problems with the existing dental implant systems. Firstly, the actual use for a given design and indication is not always followed according to the product claims. This can result in incorrect treatment or even worse, a continuous maltreatment or not optimal treatment.

Clinically, inappropriate selection may lead to poor implant stability and unacceptably high bone stresses, which can lead to failure, necrosis, fracture, etc. One example is the use of the Nobel Biocare Mk IV implant in dense bone.

Furthermore, development of new products to adjust the function or clinical procedure, e.g. to allow a new indication, leads to an even greater increase in the assortment of products.

Thus, the problems concern both the function of the implants as well as the handling and ordering situation for the clinician. This design adaptation leads undoubtedly to an increase in assortment leading to higher stock levels and thus higher working capital.

Thirdly, when a cylindrical implant is manufactured a negative tolerance is commonly introduced for the diameter difference between the apical and coronal threaded portion in order to avoid the implant failing to seat during insertion in medium to hard bone but the stability will be poorer in soft bone.

Thread cutting implants have, in the past, been designed to maximise cutting efficiency by increasing the length of the cutting edge, increasing the volume of the bone chip collecting chambers and introducing relief planes in relation to the cutting edge to provide increased contact force. Clinical problems have arisen during placement of these types of implants. Such problems include poor alignment between the thread cut in bone and the cylindrical preparation hole which can lead to poor implant stability. The malalignment may result from a decrease in the circumferential threaded area due to the presence of the cutting chamber and the relief planes. The consequential result can be poor implant to bone contact manifested clinically as wobbling during placement.

Generally, when placing an implant in bone, the diameter of the lower part of the implant is less than the diameter of the prepared cylindrical bore hole. However, in order to obtain optimum stability in, for example, soft trabecular bone, for example in the maxilla, the prepared bore hole can be as small as possible and therefore smaller than the threaded portion of the implant, leading to increased bone compression a so called under preparation.

The normal clinical procedure in an alveolar ridge is to prepare a bore hole which is smaller than the diameter of the implant body regardless of the distance from the apical end. Hence the implant, engages the bone along its entire length. This procedure includes a tapered implant in a cylindrical bore, which is distinct from that described in U.S. Pat. No. 5,427,527.

There has therefore clearly been a long felt need for an implant system which can be adapted to the actual situation by design changes and/or in combination with changes in instrumentation and/or surgical procedures. An object of this invention is to provide a universal implant which is suitable for placement and achieves optimal anchorage in either soft or hard bone. This is achieved by providing an implant which is designed to reduce high levels of compressive stress by provision of a supplementary cutting feature, during and after insertion into hard bone, but is designed for increased insertion torque when inserted into soft bone in order to obtain optimum implant stability.

SUMMARY OF THE INVENTION

Thus, according a first aspect of the invention we provide an implant for anchoring a tightly fitting prosthesis, said implant comprising an externally threaded implant body intended to be screwed into bone using an insertion tool, the body having a first end and a second, apex, end, said first end being provided with an internal open ended axial bore, the implant being tapered such that the apex end is smaller in diameter than the first end characterised in that the taper is not greater than 2° and the implant is provided with an incremental cutting face.

In an especially preferred embodiment the implant is also provided with an annular undercut region which is adapted to act as a thread cutting member. Preferably the implant is provided with a plurality of such regions, for example, three such regions.

The incremental cutting face may preferentially be a longitudinal cutting groove. The apex end of the cutting groove is preferably adjacent the apex end of the body member. The apex end of the cutting groove preferably overlaps the annular undercut region. In the most preferred embodiment, the apex region of the body member is provided with three equally sized cut away regions. Thus, the apex end of the implant is such that the implant exhibits three raised regions and three troughs, preferably wherein each cutting groove is positioned within a respective raised region.

The extremely small tapering of threaded portion is in terms of diameter difference from the apex to the increasing diameter towards the flange, ranging from 0.05 to 0.20 mm. The tapering can also be described by using degrees which will be in the range of 0.3 to 2 degrees but preferably between 0.4 and 2 degrees. Substantially, the whole of the threaded portion may be tapered or, alternatively, only a portion may be tapered, e.g. only the apical portion may be tapered.

The incremental cutting face may be in the form of one edge of a groove which extends in the threaded portion in the axial direction from the apex towards the flange and can have different and/or varying cross-sections but mainly protrudes only to the depth of a single thread, the so called thread height which preferably is 0.15 to 0.6 mm and especially 0.2 to 0.4 mm. The depth of the groove may vary depending, inter alia, upon the application and/or the bone tissue used.

The implant of the invention may be utilised in a variety of technical areas or applications. However, we especially provide an implant as hereinbefore described wherein the implant is a dental implant.

Alternatively, we provide an implant as hereinbefore described wherein the implant is an orthopaedic implant, such as a spinal implant, or other such implants, for example, a cranio facial implant.

A particular advantage of the implant assembly as hereinbefore described is that the implant may be a titanium implant. According to a further aspect of the invention we provide an arrangement for a threaded implant designed to permit anchoring of the implant in soft or hard tissue, the implant being designed for anchoring a tightly fitting prosthesis, said implant comprising an externally threaded implant body intended to be screwed into bone using an insertion tool, the body having a first end and a second, apex, end, said first end being provided with an internal open ended axial bore, the implant being tapered such that the apex end is smaller in diameter than the first end, characterised in that the taper is not greater than 2° and the implant is provided with an incremental cutting face.

The arrangement may have geometrical means which are co-operating with the cutting grooves of the apical portion as, e.g., spaces or chambers. The geometrical means may be reaching from the apical portion to the flange, which is at the end of the implant distal to the apex end, alternatively, the geometrical means may be reaching from the apical portion to preferably one or more complete threads from the flange. The implant may exhibit more than one thread, i.e. a multiple thread pattern.

To develop an implant which achieves optimal placement in hard and soft bone, providing a low insertion torque in hard bone and provides good initial stability in soft bone, by designing the threaded portion of the implant in the following way:

A small tapering is introduced from the apex and the diameter is increased towards the flange of threaded portion. An incremental cutting face is included extending in the threaded portion in the axial direction from the apex towards the flange. Aggressive cutting edges are included by way of an annular recess in the apical region, designed for keeping the maximum of the threaded, area intact while increasing cutting ability by co-operation with the apical portion of the incremental cutting face through the function of relief volumes. The above is under the condition that the preparation of the surgical hole is made with a substantially cylindrical drill with the option that the threads could be multiple. A screw tap may optionally be necessary when used in connection with extremely hard bone.

The problem with using cylindrical implants in cylindrical holes is that the thread in the bone which is, in most cases, created by the thread cutting part of the implant is abraded as the implant is screwed in, and with this abrasion bone is removed mainly at the inlet/mouth of the hole in the bone. This can result in a reduced initial implant stability especially in, weak/soft bone. A significant problem is development of heat which occurs during the conical preparation. Since a tapered drill cuts along the whole periphery, relatively great heat is generated, leading to bone necrosis and this negative effect can result in failure. This can be amplified further by the fact that the cutting geometry of a tapered drill results in a low surface pressure occurring at the cutting face and decreased efficiency. This results in a higher ratio of abrasion to chip formation.

This significantly reduces the possibilities of successful osseointegration. The object of the present invention is to solve the above problems among others.

The said use of a screw connection on the implant involves the screwing and unscrewing of screws. This represents a risk of introducing rotational mobility between an implant and the bone which may lead to failure.

This applies in particular if the implants are fitted in bone which is of weak/soft quality. The above loosening problems are especially pronounced in the case of implants with a thread which is circularly symmetrical. In most threaded implants, it is of course possible to arrange cut-outs or annular undercut regions at the apex, which are intended both to cut threads and to contribute to the rotational stability. There are also implants with transverse holes for bone to grow into. A common feature of these known constructions is that the recesses and holes are relatively small when seen in relation to the threaded area of the implant. Since the surface area of the recesses or holes is small, deformation or break-up of the ingrown bone can easily take place upon torsional loading. In addition, the holes and recesses are situated at the very front of the tip where in most cases the quality of the bone (its hardness) is poor, for example, in unicortical anchorage. There is also an inherent weakness in that the holes and recesses reduce the threaded area of the implant. It must be emphasised here that it is desirable to maximise the threaded area for effective transfer of the functional load from the tooth prosthesis or tooth bridge down to the bone. This applies in particular in the case of soft bone.

If the implant does not sit with sufficient stability in the bone directly after insertion, microscopic movements can occur between the implant and the surrounding bone tissue, for example when the implant is bent, which can happen when the bone is exposed to mastication loads or when the patient has a conventional tooth prosthesis which presses on the gum above the implant. These microscopic movements can impair healing and/or bone formation leading to failure of the implant. It is therefore important for the implant to have sufficient initial stability.

An important precondition for being able to implement the above mentioned methods is to create the conditions for obtaining optimum direct bone contact with the implant at placement during the healing in process. It is essential in this connection to perform meticulous surgery when fitting the implants. The cylindrical hole for the implant must be drilled with great precision and in this connection it is of the utmost importance that the temperature in the bone does not become too high. These requirements have hitherto meant that both the drilling and the fitting of the implant have been carried out with the hole forming and tightening instruments being operated at low speed. The speed of rotation which is normally employed when fitting implants is 15-25 rpm. This means that the time required for fitting an implant can amount to 1 minute or more. During this time, it is necessary for the surgeon fitting the implant to keep a very steady hand so as to ensure that any fine bone trabeculae surrounding the hole are not deformed, broken up or compressed. Wobbling movements of the instrument during tightening pose risks of deformation and break-up.

According to a further aspect of the invention we provide a method of mounting an implant in a prepared substantially cylindrical bore in tissue comprising the steps of:

(i) preparing a cylindrical bore in soft or hard tissue
(ii) inserting a tapered implant as hereinbefore described.

During insertion in soft bone however some of the cutting means do not obtain sufficient surface contact pressure in order to cut effectively, leading to a substantial increase in insertion torque during the insertion procedure due to the compression of the bone.

The method may comprise an implant being inserted in a prepared cylindrical bore, and where the same type of implant design is used whether in hard or soft bone without losing the advantages of an implant design specifically made either for hard bone and therefore experiencing relatively low insertion torque, or for soft bone where a substantially increasing insertion torque is regarded as favourable. The principle behind the method is that the cutting means of the implant are designed to all function when insertion is being made in hard bone but, in soft bone, the incremental cutting grooves will be less effective.

The implant which is both suitable for hard and soft bone by providing low insertion torque in hard bone and good initial stability in soft bone by adjusting the threaded portion of the implant is based on a tapered threaded portion.

The annular undercut region in the apical region can have a different cutting angle provided that the maximum of the threaded area is kept intact while increasing cutting ability by co-operation with the apical portion of the cutting grooves through the function of relief volumes which decreases any tendency to wobbling. In order to have a sharp edge but not a weak apex a cutting flute with a double radii can be introduced to increase the bulk material. One embodiment is that the threads could be multiple.

Thus the characteristic geometrical features may be summarised as follows:
  small tapering;
  cutting grooves along the threaded side for multiple purposes;
  cutting in order to compensate for the increased diameter; and
  relief area for the main apical cutting edges in order to increase the pressure on the cutting edge and thereby providing less cutting resistance and hence lower insertion torque;
  double threads for decreased insertion time and maintaining proven thread profile;
  insertion in a cylindrical hole prepared in the jawbone.

Similarly, the characteristic functional features may be summarised as follows:
  Superb insertion properties for hard to soft bone;
  meaning for hard bone good cutting properties and thereby low insertion torque (comparable to Mk III (machined or TiUnite)) resulting in a high level of bone to implant contact;
  decreased wobbling tendency.
  and for soft bone:
  increased insertion torque as the implant is being inserted meaning that the axial grooves are not cutting since the softer bone will not provide enough pressure between bone cutting edge of the grooves and only providing rotational stability.

A further advantage is that, inter alia, in use, unlike the Niznick system of the prior art, the whole length of the implant of the present invention will contact the sides of the bore hole into which the implant is introduced.

Other advantages and features will be readily available from the following description of the preferred embodiments, the drawings, and claims.

BRIEF DESCRIPTION OF THE DRAWINGS

The invention will now be described with reference to the accompanying example and drawings in which.

DETAILED DESCRIPTION OF EMBODIMENTS

Figure 1:
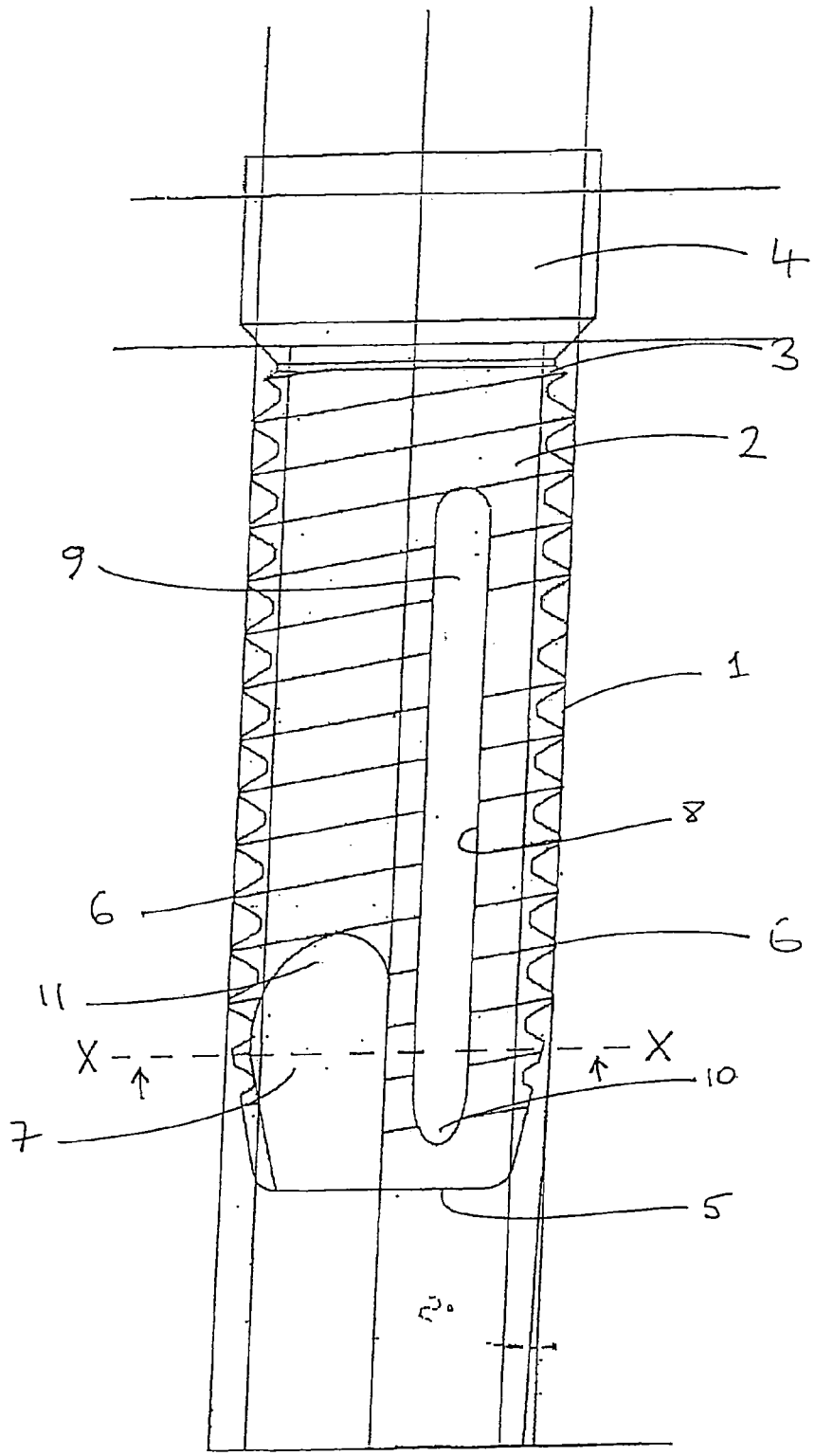
FIG. 1 is a perspective view of an implant of the invention.

Referring to FIG. 1 an implant (1) of the invention comprises a longitudinal body member (2) provided at a first end (3) with a flange head (4) which has an arrangement (not shown) adapted to engage with a prostheses, for example, a dental prosthesis. The body member (2) is tapered such that a second end or apex end (5) distal to the first end (3) is narrower in diameter than the first end (3). In addition the body member (2) is provided with an external thread (6). The second end (5) of the body member is provided with an undercut region (7).

The body member (2) is also provided with at least one incremental cutting face (8) in the form of a longitudinal, substantially linear cutting groove (9). The apex end (10) of the incremental cutting face (8) is adjacent the apex end (5) of the body member (2). Longitudinally, the apex end (10) of the incremental cutting face (8) overlaps the end (11) of the annular undercut region (7) distal to the apex end (5) of the implant. As can be seen from FIG. 2, the axial edge of the undercut region (7) adjacent to the apex end (10) of the incremental cutting face has a straight edge, whereas the other side of the undercut region (7) has a curved axial edge.

Figure 2:
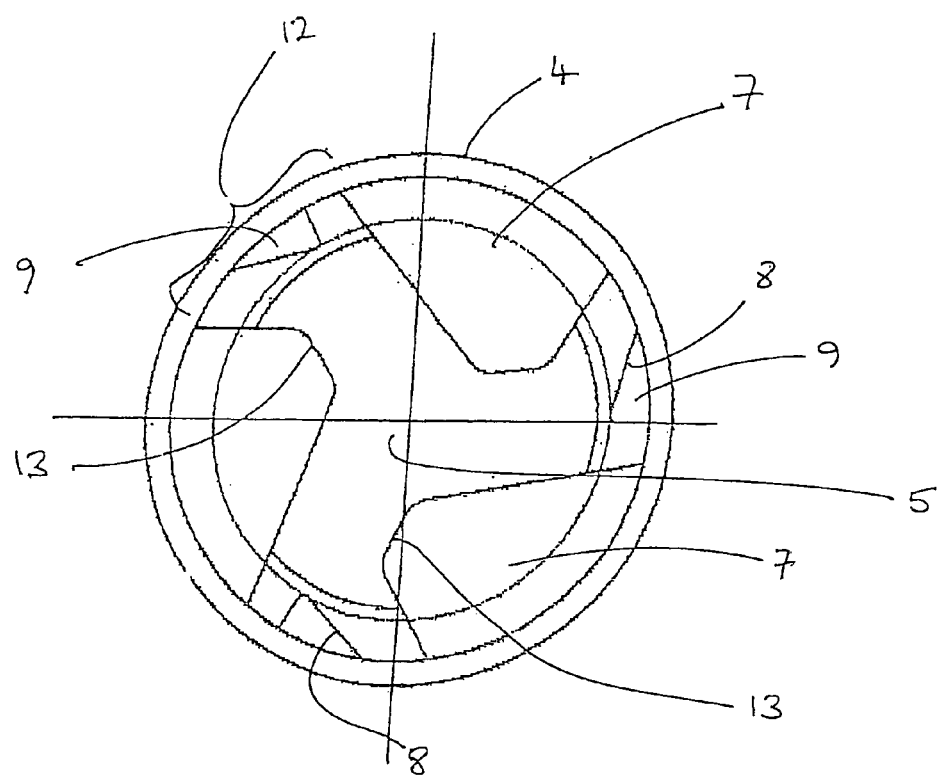
FIG. 2 is an end apex view of an implant of FIG. 1, viewed as a cross-section along X-X.

Referring to FIG. 2, in the preferred embodiment of the invention, the body member (2) is provided with three equally sized annular undercut regions (7) and three longitudinal substantially linear cutting grooves (9). Thus, in the cross-sectional view of the implant (I) the implant (1) exhibits three non-undercut regions (12) and three troughs being the undercut regions (7). The longitudinal cutting grooves (9) are positioned one within each raised region (12).

The annular undercut region (7) is provided with a recessed wall (13) within the cavity of the undercut region (7). Thus, the annular undercut region (7) comprises a cutting edge (14), and a leading edge (15) at either side of the recessed wall (13). In the implant of the present invention, the rear cavity wall (13) is sufficient to distinctly separate the leading edge and the cutting edge, although the overall angle between the cutting wall and trailing walls is less than 90°. Thus, the screw body (15) between undercut regions (7) are thicker than conventional implants.

The implant body member is tapered, such that the taper is not greater than 2°, the apex end being narrower than the distal, flanged end.

In use, a cylindrical hole is drilled into the bone of a patient, the tapered implant is place in the hole and screwed clockwise into the hole.

This provides a number of advantages, inter alia, that the region between the cut way regions may be thicker than conventional devices, therefore enabling materials such as titanium of different grades and purity to be used.

Example 1

Comparative Tests

Tests were carried out to examine the cutting characteristics of an implant according to the invention (Test) compared to existing products (Nobel Biocare).

Figure 3:
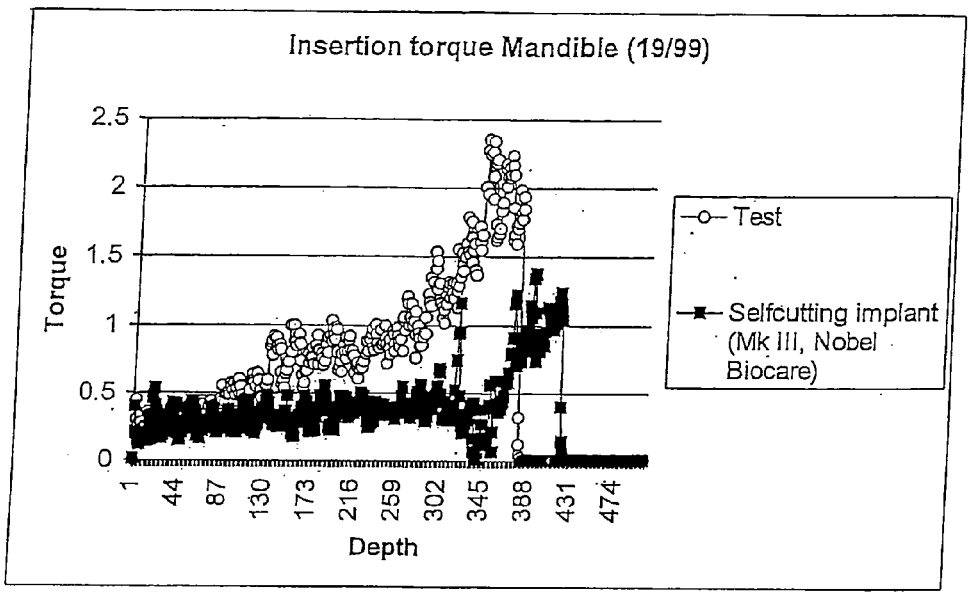
FIG. 3 is a comparison in a mandible (dense bone) with the Mk III implant which is an extremely self-cutting implant.

Graph 1 as shown in FIG. 3, is a comparison in a mandible (dense bone) with the Mk III implant which is an extremely self cutting implant. The two implants follow the same pattern, with the Test on somewhat higher, but totally acceptable, levels of insertion torque.

Figure 4:
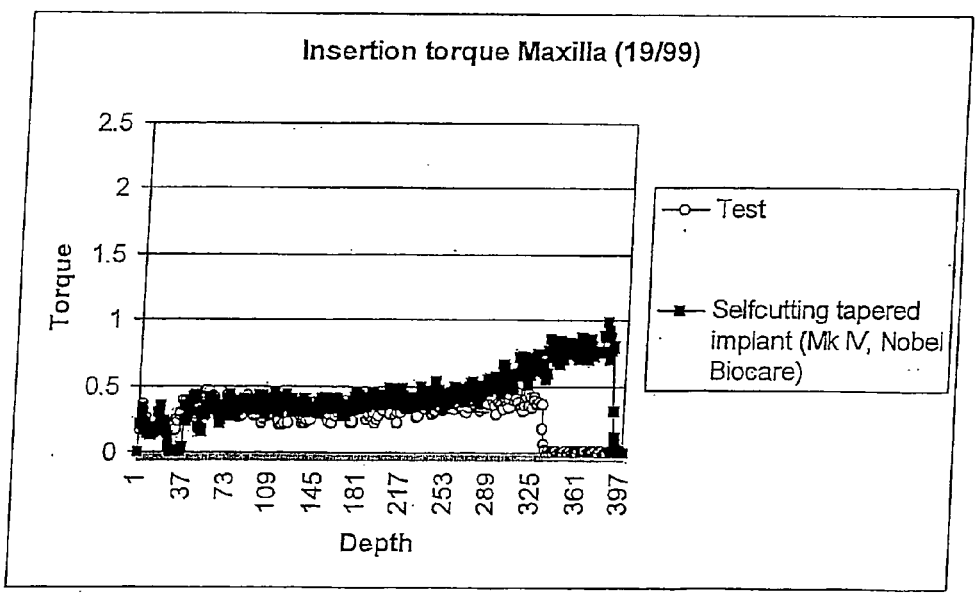
FIG. 4 is a comparison in a maxilla (soft bone) with the Mk IV implant, which is a tapered implant made for placement in soft bone.

Graph 2 as shown in FIG. 4, is a comparison in a maxilla (soft bone) with the Mk IV implant, which is a tapered implant made for placement in soft bone. Again the Test implant follows the same characteristics and have similar insertion torque as an existing implant, but now with a design for placement in soft bone.

The invention claimed is:

1. An implant for anchoring a tightly fitting prosthesis, comprising:
   an implant body having external threads and being configured to be screwed into bone using an insertion tool,
   the body defining an axial direction and having
      a first end, and
      a second, apex end,
   said first end having an internal open ended axial bore,
   the implant being tapered such that the apex end is smaller in diameter than the first end, wherein the taper is not greater than 2°,
   wherein the implant body is provided with a plurality of incremental cutting faces and a plurality of thread cutting members separate from the incremental cutting faces,
   wherein the incremental cutting faces each comprise an axially extending groove in the external threads defining a substantially linear cutting groove in the threads,
   wherein the thread cutting members each comprise an annular undercut region in the apex end of the implant body, the annular undercut region providing a relief volume and being defined by a cutting edge and a trailing edge at either side of a recessed wall, wherein raised regions are formed between the cutting edge of one annular undercut region and the trailing edge of an adjacent annular undercut region, and
   wherein the incremental cutting faces and the thread cutting members overlap one another in the axial direction of the implant body such that an apex portion of each linear cutting groove is positioned within a raised region.

2. An implant according to claim 1 wherein the implant body comprises three undercut regions.

3. An implant according to claim 1 wherein an apex end of the incremental cutting face is adjacent the apex end of the body member.

4. An implant according to claim 1 wherein the axially extending groove has a varying cross-section along its length.

5. An implant according to claim 2 wherein the apex end of the implant body is configured such that the implant exhibits three raised regions and three troughs.

6. An implant according to claim 1 wherein the implant is a dental implant.

7. An implant according to claim 1 wherein the implant is an orthopaedic implant.

8. An implant according to claim 1 wherein the implant is a titanium implant.

9. An implant according to claim 1 wherein the implant is configured for insertion into hard bone and soft bone.

10. An implant according to claim 1 wherein the overall angle between the cutting edge and the leading edge is less than 90° and wherein the angles between the cutting edge and the recessed wall, and between the leading edge and the recessed wall are each greater than 90°.

11. An implant according to claim 1, wherein only the apex end of the implant is tapered.

12. An apparatus for a threaded implant configured to permit anchoring of the implant in soft or hard tissue, the implant comprising an implant body having external threads and being configured to be screwed into bone using an insertion tool,
the body defining an axial direction and having
a first end, and
a second, apex end,
said first end having an internal open ended axial bore,
the implant being tapered such that the apex end is smaller in diameter than the first end, wherein the taper is not greater than 2°,
wherein the implant body is provided with a plurality of incremental cutting faces and a plurality of thread cutting members separate from the incremental cutting faces,
wherein the incremental cutting faces each comprise an axially extending groove in the external threads defining a substantially linear cutting groove in the threads,
wherein the thread cutting members each comprise an annular undercut region in the apex end of the implant body, the annular undercut region providing a relief volume and being defined by a cutting edge and a trailing edge at either side of a recessed wall, wherein raised regions are formed between the cutting edge of one annular undercut region and the trailing edge of an adjacent annular undercut region, and
wherein the incremental cutting faces and the thread cutting members overlap one another in the axial direction of the implant body such that an apex portion of each linear cutting groove is positioned within a raised region.

13. An apparatus according to claim 12 wherein the implant body comprises more than one thread pattern.

14. An apparatus according to claim 13 wherein the incremental cutting face reaches from adjacent the apex region to a flange at the first end.

15. An apparatus according to claim 12 wherein the implant body comprises a plurality of undercut regions such that each undercut region has a triple sided profile in the plane perpendicular to the longitudinal axis.

16. An apparatus according to claim 12 wherein the apparatus is configured for use in hard bone and soft bone.

17. A method of mounting an implant in a prepared substantially cylindrical bore in tissue comprising:
preparing a cylindrical bore in soft or hard tissue; and
inserting into the bore a tapered implant comprising an externally threaded implant body configured to be screwed into bone using an insertion tool, the body defining an axial direction and having a first end, and a second, apex end, said first end having an internal open ended axial bore,
the implant being tapered such that the apex end is smaller in diameter than the first end, wherein the taper is not greater than 2°,
wherein the implant body is provided with a plurality of incremental cutting faces and a plurality of thread cutting members separate from the incremental cutting faces,
wherein the incremental cutting faces each comprise an axially extending groove in the external threads defining a substantially linear cutting groove in the threads,
wherein the thread cutting members each comprise an annular undercut region in the apex end of the implant body, the annular undercut region providing a relief volume and being defined by a cutting edge and a trailing edge at either side of a recessed wall, wherein raised regions are formed between the cutting edge of one annular undercut region and the trailing edge of an adjacent annular undercut region, and
wherein the incremental cutting faces and the thread cutting members overlap one another in the axial direction of the implant body such that an apex portion of each linear cutting groove is positioned within a raised region.

18. A method according to claim 17 wherein the implant is inserted in a prepared cylindrical bore, and wherein the implant experiences low insertion torque in hard bone, or an increasing insertion torque for soft bone.

19. A method according to claim 17 wherein the bore is a cylindrical bore.

20. A method according to claim 17 wherein the bone is hard bone and the bone experiences low insertion torque.

21. A method according to claim 17 wherein the bone is soft bone and the bone experiences increasing insertion torque.

22. A method according to claim 17 wherein the bone is a jaw bone.

23. An implant kit comprising:
an implant configured for insertion into a cylindrical bore comprising an externally threaded implant body configured to be screwed into bone using an insertion tool, the body defining an axial direction and having a first end, and a second, apex end, said first end having an internal open ended axial bore,
the implant being tapered such that the apex end is smaller in diameter than the first end, wherein the taper is not greater than 2°,
wherein the implant body is provided with a plurality of incremental cutting faces and a plurality of thread cutting members separate from the incremental cutting faces, wherein the incremental cutting faces each comprise an axially extending groove in the external threads defining a substantially linear cutting groove in the threads,
wherein the thread cutting members each comprise an annular undercut region in the apex end of the implant body, the annular undercut region providing a relief volume and being defined by a cutting edge and a trailing edge at either side of a recessed wall, wherein raised regions are formed between the cutting edge of one annular undercut region and the trailing edge of an adjacent annular undercut region, and wherein the incremental cutting faces and the thread cutting members overlap one another in the axial direction of the implant body such that an apex portion of each linear cutting groove is positioned within a raised region;
a tool adapted for carrying and inserting the implant; and
a drill for cutting the cylindrical bore.

24. An implant kit according to claim 23 wherein the kit is a dental implant kit.

* * * * *